US012724019B2

(12) United States Patent
Hao et al.

(10) Patent No.: US 12,724,019 B2
(45) Date of Patent: Sep. 1, 2026

(54) METHOD AND APPARATUS FOR DETERMINING HARDNESS OF RAW WATER OF WATER SOFTENING DEVICE

(71) Applicants: FOSHAN MIDEA CHUNGHO WATER PURIFICATION EQUIPMENT CO., LTD., Foshan (CN); MIDEA GROUP CO., LTD., Foshan (CN)

(72) Inventors: Zhipeng Hao, Foshan (CN); Chenghuan Hu, Foshan (CN); Pu Qing, Foshan (CN); Bo Zhang, Foshan (CN); Ziming Gong, Foshan (CN); Rensheng Huang, Foshan (CN); Yuedong Zheng, Foshan (CN); Yumin Liao, Foshan (CN)

(73) Assignees: FOSHAN MIDEA CHUNGHO WATER PURIFICATION EQUIPMENT CO., LTD., Foshan (CN); MIDEA GROUP.CO., LTD., Foshan (CN)

( * ) Notice: Subject to any disclaimer, the term of this patent is extended or adjusted under 35 U.S.C. 154(b) by 389 days.

(21) Appl. No.: 18/564,095

(22) PCT Filed: Apr. 11, 2023

(86) PCT No.: PCT/CN2023/087679

§ 371 (c)(1),
(2) Date: Nov. 26, 2023

(87) PCT Pub. No.: WO2023/231587

PCT Pub. Date: Dec. 7, 2023

(65) Prior Publication Data

US 2025/0085267 A1 Mar. 13, 2025

(30) Foreign Application Priority Data

May 30, 2022 (CN) ......................... 202210605813.8

(51) Int. Cl.
*G01N 33/18* (2006.01)
*C02F 1/42* (2023.01)

(52) U.S. Cl.
CPC ............ *G01N 33/1853* (2013.01); *C02F 1/42* (2013.01); *C02F 2209/055* (2013.01)

(58) Field of Classification Search
CPC .. G01N 33/1853; C02F 1/42; C02F 2209/055
(Continued)

(56) References Cited

U.S. PATENT DOCUMENTS 10,501,343 B1 * 12/2019 Hoefferle ................ C02F 1/008
12,330,973 B2 * 6/2025 Christensen .......... H04W 84/18
(Continued)

FOREIGN PATENT DOCUMENTS

CN 104746288 A 7/2015
CN 105092804 A 11/2015
(Continued)

OTHER PUBLICATIONS

EESR received in EP Application No. 23805838.2; mailed Apr. 4, 2024.
(Continued)

*Primary Examiner* — Zhen Y Wu
(74) *Attorney, Agent, or Firm* — K&L Gates LLP

(57) ABSTRACT

A method and an apparatus for determining hardness of raw water of a water softening device. The method includes: obtaining a correspondence between a geographical area and the hardness of raw water; and determining target hardness of raw water of the water softening device based on a target geographical area where the water softening device is located and the correspondence; the correspondence is obtained by detecting hardness of raw water of respective geographical areas and associating each of the respective geographical areas with a detection result of the hardness of
(Continued)

raw water corresponding to each of the respective geographical areas.

15 Claims, 2 Drawing Sheets

(58) Field of Classification Search
USPC .................................................... 702/30
See application file for complete search history.

(56) References Cited

U.S. PATENT DOCUMENTS

2001/0039465 A1* 11/2001 Schultz .................. G05B 15/02 700/282
2012/0078722 A1* 3/2012 Van Oosterwijck .......................... G06Q 30/0613 709/219
2014/0231348 A1* 8/2014 Sackstein .................. C02F 1/32 422/186.04
2017/0004558 A1* 1/2017 Abramowitz ...... G06Q 30/0631
2018/0270548 A1* 9/2018 Richter .................... H04Q 9/00
2018/0318767 A1* 11/2018 Roitel .................... B01D 61/58
2019/0144301 A1* 5/2019 Branum .................. C02F 1/008 210/739
2020/0316657 A1* 10/2020 Erickson ................. B08B 9/032
2021/0293770 A1 9/2021 Qin et al.
2022/0194819 A1* 6/2022 Zhao ....................... C02F 1/008
2023/0064773 A1* 3/2023 Christensen .............. C02F 1/42
2024/0109795 A1* 4/2024 Bakow ...................... C02F 1/42

FOREIGN PATENT DOCUMENTS

CN 107818328 A 3/2018
CN 109213215 A 1/2019
CN 109319885 A 2/2019
CN 109948715 A 6/2019
CN 110255724 A 9/2019
CN 105847434 B 10/2019
CN 110991530 A 4/2020
CN 112116080 A 12/2020
CN 113408112 A 9/2021
CN 114074978 A 2/2022
CN 114547229 A 5/2022
CN 114994274 A 9/2022
DE 102014101285 A1 8/2015

OTHER PUBLICATIONS

Second office action Received in Chinese priority application CN202210605813.8; mailed Jan. 2, 2024.
ISR received in PCT/CN2023/087679; mailed Jun. 21, 2023.
First office action received in Chinese priority application No. 202210605813.8; mailed Apr. 19, 2023.
"Analysis on total hardness of drinking water in rural areas of Wuzhou City from 2015-2019"; May 31, 2021, by Wei Lili.

* cited by examiner

METHOD AND APPARATUS FOR DETERMINING HARDNESS OF RAW WATER OF WATER SOFTENING DEVICE

CROSS-REFERENCES TO RELATED APPLICATIONS

The present disclosure is a national phase application of International Application No. PCT/CN2023/087679, filed on Apr. 11, 2023, which claims priority to Chinese Patent Applications No. 202210605813.8, filed on May 30, 2022, which is hereby incorporated by reference in its entirety.

FIELD

The present disclosure relates to the field of water softening device, in particular to a method and an apparatus for determining hardness of raw water of a water softening device.

BACKGROUND

A water softener can soften high-hardness water into soft water by replacing calcium ions and magnesium ions in the water with sodium ions, which has effects of prolonging a service life of a rear-end water-associated appliance, beautifying, caring skin and caring for clothes.

When a user installs a water softener for the first time, conventional hardness testing modes such as "titration method" and "reagent method" are cumbersome, highly specialized, and requires a professional testing device. As such, it is unable to accurately determine hardness of raw water, which is the most critical parameter of the water softener. This causes softening effect of the water softener to be less than expected, and fails to achieve desired effect. Further, long-term usage will also cause damage to the expensive water softener.

SUMMARY

The present disclosure aims to address at least one of the problems above. The present disclosure provides a method for determining hardness of raw water of a water softening device, which avoids defects such as cumbersome operations and inaccurate detection results caused by on-site testing of the hardness of raw water, and improves the efficiency and accuracy of determining the hardness of raw water.

The present disclosure further provides an apparatus for determining hardness of raw water of a water softening device.

The present disclosure further provides an electronic device, a non-transitory computer-readable storage medium and a computer program product.

An embodiment of the present disclosure provides a method for determining hardness of raw water of a water softening device, including:

- obtaining a correspondence between a geographical area and the hardness of raw water; and
- determining target hardness of raw water of the water softening device based on a target geographical area where the water softening device is located and the correspondence,
- where the correspondence is obtained by detecting hardness of raw water of respective geographical areas and associating each of the respective geographical areas with a detection result of the hardness of raw water corresponding to each of the respective geographical areas.

In the method for determining the hardness of raw water of the water softening device, by determining the target hardness of raw water of the water softening device based on the target geographical area where the water softening device is located and the correspondence, defects such as cumbersome operations and inaccurate detection results caused by on-site testing of the hardness of raw water are avoided, and the efficiency and accuracy of determining the hardness of raw water are improved.

According to an embodiment of the present disclosure, determining target hardness of raw water of the water softening device based on the target geographical area where the water softening device is located and the correspondence includes:

- determining, in accordance with a determination that no hardness of raw water matched with the target geographical area is included in the correspondence, a first geographical area closest to the target geographical area from the correspondence;
- determining first hardness of raw water corresponding to a first geographical area from the correspondence based on the first geographical area; and
- assigning the first hardness of raw water to the target hardness of raw water.

In the method for determining the hardness of raw water of the water softening device, by assigning, in accordance with inability to determine the hardness of raw water of the geographical area where the water softening device is located, the hardness of raw water of the geographical area closest to the geographical area where the water softening device is located to the raw water of the water softening device, the hardness of raw water of the water softening device can still be very accurate, and the normal use of the water softening device is ensured.

According to an embodiment of the present disclosure, determining target hardness of raw water of the water softening device based on the target geographical area where the water softening device is located and the correspondence includes:

- determining, in accordance with a determination that no hardness of raw water matched with the target geographical area is included in the correspondence, second geographical areas that are within a preset distance range from the target geographical area from the correspondence;
- determining second hardness of raw water corresponding to each of the second geographical areas from the correspondence based on each of the second geographical areas; and
- assigning an average value of all second hardness of raw water to the target hardness of raw water.

In the method for determining the hardness of raw water of the water softening device, by assigning, in accordance with inability to determine the hardness of raw water of the geographical area where the water softening device is located, the average value of the hardness of raw water of the geographical areas closest to the geographical area where the water softening device is located to the raw water of the water softening device, the hardness of raw water of the water softening device can still be very accurate, and the normal use of the water softening device is ensured.

According to an embodiment of the present disclosure, determining target hardness of raw water of the water softening device based on the target geographical area where the water softening device is located and the correspondence includes:

determining, in accordance with a determination that no hardness of raw water matched with the target geographical area is included in the correspondence, second geographical areas that are within a preset distance range from the target geographical area from the correspondence;

determining a third geographical area among second geographical areas, and determining third hardness of raw water corresponding to the third geographical area from the correspondence based on the third geographical area; and assigning the third hardness of raw water to the target hardness of raw water.

In the method for determining the hardness of raw water of the water softening device, by selecting, in accordance with inability to determine the hardness of raw water of the geographical area where the water softening device is located, one of the hardness of raw water of the geographical areas closest to the geographical area where the water softening device is located as the raw water of the water softening device, the hardness of raw water of the water softening device can still be very accurate, and the normal use of the water softening device is ensured.

According to an embodiment of the present disclosure, determining the third geographical area from the second geographical areas includes any one of the followings: determining, randomly, a third geographic area from second geographic areas; and assigning a second geographical area that meets a preset condition among the second geographical areas to the third geographical area, where the preset condition includes any one of the followings:

a raw water supplier in the second geographical area is the same as a raw water supplier in the target geographical area; and a raw water source in the second geographical area is the same as a raw water source in the target geographical area;

By selecting, from the second geographic areas, a second geographic area in which the raw water supplier is the same as the raw water supplier in the target geographical area, or the raw water source is the same as the raw water source in the target geographical area as the third geographical area, the final determined hardness of raw water of the water softening device can still be highly accurate, and the normal use of the water softening device is ensured.

According to an embodiment of the present disclosure, obtaining the correspondence between a geographical area and the hardness of raw water includes any one of the followings:

receiving the correspondence between the geographical area and the hardness of raw water transmitted from a server; and receiving the correspondence between the geographical area and the hardness of raw water transmitted from a terminal.

According to an embodiment of the present disclosure, the method further includes:

obtaining updated information of the correspondence between the geographical area and the hardness of raw water, and updating the correspondence between the geographical area and the hardness of raw water with the updated information.

An embodiment of the present disclosure provides an apparatus for determining hardness of raw water of a water softening device, including:

an obtaining device for obtaining a correspondence between a geographical area and the hardness of raw water; and a determining device for determining target hardness of raw water of the water softening device based on a target geographical area where the water softening device is located and the correspondence, where the correspondence is obtained by detecting hardness of raw water of respective geographical areas, and associating each of the respective geographical areas with a detection result of the hardness of raw water corresponding to each of the respective geographical areas.

In the apparatus for determining the hardness of raw water of the water softening device, by determining the target hardness of raw water of the water softening device based on the target geographical area where the water softening device is located and the correspondence, defects such as cumbersome operations and inaccurate detection results caused by on-site testing of the hardness of raw water are avoided, and the efficiency and accuracy of determining the hardness of raw water are improved.

An embodiment of the present disclosure provides an electronic device, including a processor and a memory storing a computer program executable on the processor, and the computer program, when executed by the processor, causes the electronic device to perform the method for determining hardness of raw water of a water softening device mentioned above.

An embodiment of the present disclosure provides a non-transitory computer-readable storage medium storing a computer program, and the computer program, when executed by a processor, causes the processor to perform the method for determining hardness of raw water of a water softening device mentioned above.

An embodiment of the present disclosure provides a computer product, including a computer program, where the computer program, when executed by a processor, causes the processor to perform the method for determining hardness of raw water of a water softening device mentioned above.

One or more solutions in the embodiments of the present disclosure mentioned above have at least one of the following effects:

defects such as cumbersome operations and inaccurate detection results caused by on-site testing of the hardness of raw water are avoided, and the efficiency and accuracy of determining the hardness of raw water are improved.

Further, the hardness of raw water of the water softening device can still be very accurate, and the normal use of the water softening device is ensured in accordance with inability to determine the hardness of raw water of the geographical area where the water softening device is located.

The embodiments of the present disclosure will be partially given in the following description, and some thereof will become clear from the following description, or be understood through the practice of the present application.

BRIEF DESCRIPTION OF THE DRAWINGS

In order to clearly illustrate the solutions according to the present application or the related art, the accompanying drawings used in the description of the embodiments of the present application or the related art are briefly introduced below. It should be noted that the drawings in the following description are of only part embodiments of the present application.

DETAILED DESCRIPTION OF THE DISCLOSURE

Embodiments of the present disclosure are further described in detail below with reference to the drawings and embodiments. The following embodiments are intended to illustrate the disclosure, but not intended to limit the scope of the disclosure.

In the description of this specification, descriptions with reference to the terms "one embodiment", "some embodiments", "examples", "specific examples", or "some examples" etc. mean that specific features, structure, material or characteristics described in conjunction with the embodiment or example are included in at least one embodiment or example of the embodiments of the present disclosure. In this specification, the schematic expressions of the above terms do not necessarily refer to the same embodiment or example. Furthermore, the feature, structures, material or characteristics described can be combined in any suitable manner in any one or more embodiments or examples. Embodiments or examples described in this specification, as well as the features of the different embodiments or examples, without conflicting each other.

Figures 1, 2:
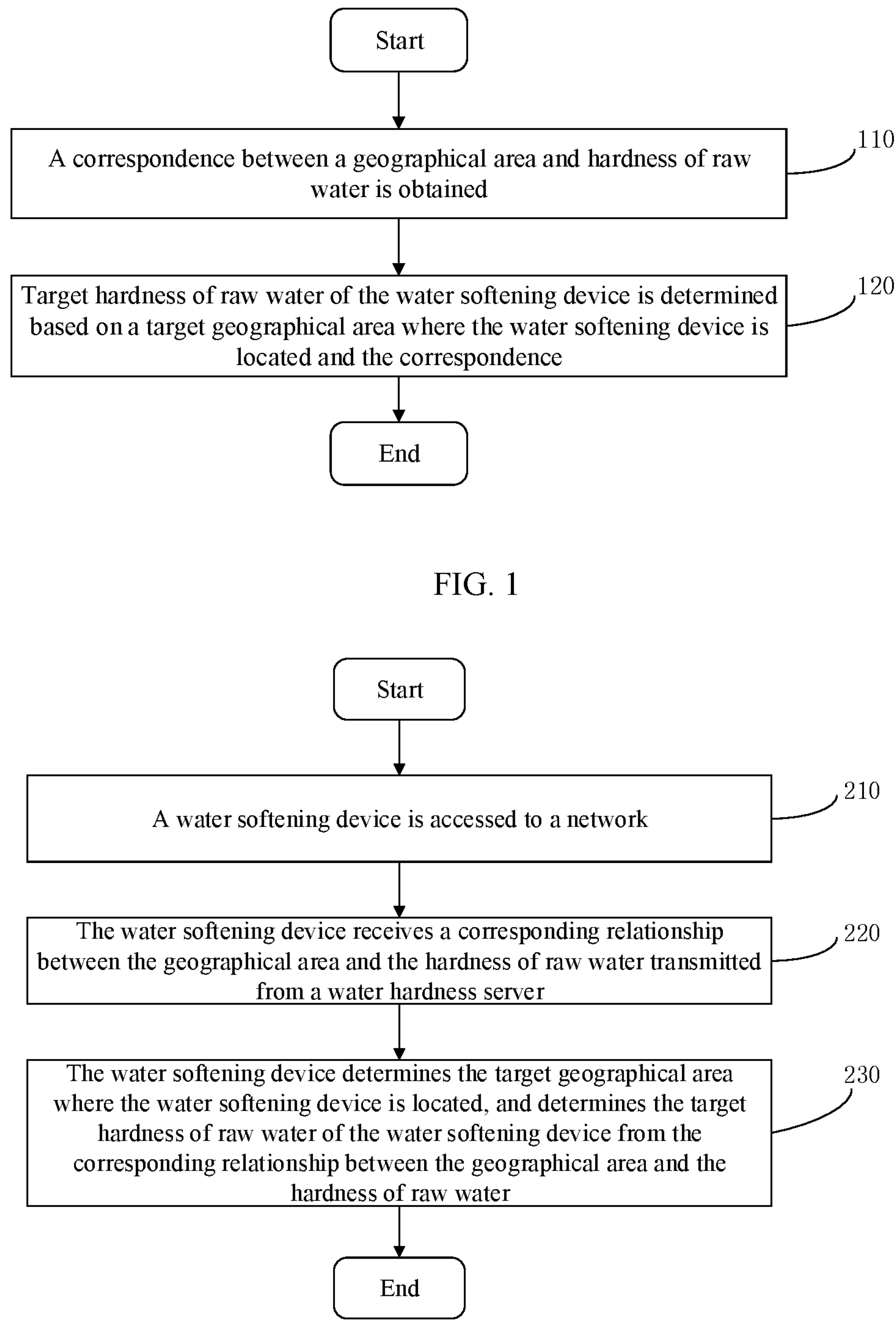
FIG. 1 is a schematic flow chart of a method for determining hardness of raw water of a water softening device according to an embodiment of the present disclosure.
FIG. 2 is a schematic flow chart of the method for determining the hardness of raw water of a water softening device according to an embodiment of the present disclosure in a water softening device installation scenario.

FIG. 1 is a schematic flow chart of a method for determining hardness of raw water of a water softening device according to an embodiment of the present disclosure. Referring to FIG. 1, the method for determining the hardness of raw water of the water softening device according to an embodiment of the present disclosure may include the following.

Block 110, a correspondence between a geographical area and the hardness of raw water is obtained.

Block 120, target hardness of raw water of the water softening device is determined based on a target geographical area where the water softening device is located and the correspondence.

The correspondence is obtained by detecting hardness of raw water of respective geographical areas and associating each of the respective geographical areas with a detection result of the hardness of raw water corresponding to each of the respective geographical areas.

It should be noted that, a sterilization control method of the water softening device according to the embodiment of the present disclosure may be performed by the water softening device.

Before block 110, the hardness of raw water of various geographical areas may be collected to form a map of hardness of raw water (correspondences between geographical areas and hardness of raw water). Various geographical areas can be divided according to a certain granularity based on actual conditions, such as provinces, cities, counties (districts), towns, villages, etc. Embodiments of the present disclosure do not specifically limit this.

The hardness of raw water samples from various geographical areas can be tested in professional water quality laboratories to ensure the accuracy of detection results of the hardness of raw water, and the tested hardness data of raw water can be uploaded to a water hardness server for storage. The water hardness server will associate the received hardness data information of raw water with the geographical area information of a sampling location corresponding to the hardness data of raw water to generate the map of hardness of raw water (a correspondence between geographical areas and hardness of raw water).

In the block 110, the water softening device can receive the correspondence between the geographical area and the hardness of raw water transmitted from the water hardness server through a Wi-Fi module of the water softening device.

In one embodiment, when the water softening device is connected to a terminal, the terminal can first obtain the correspondence between the geographical area and the hardness of raw water from the water hardness server, and then the terminal can transmit the correspondence between the geographical area and the hardness of raw water to the water softening device through Wi-Fi, Bluetooth, NFC, ZigBee, etc.

It can be understood that obtaining the correspondence between geographical areas and the hardness of raw water through various ways can significantly improve the applicability of water softening device.

After the correspondence between the geographical area and the hardness of raw water is obtained, in the block 120, a target geographical area where the water softening device is located is determined, the hardness of raw water corresponding to the target geographical area is determined from the correspondence between the geographical area and the hardness of raw water, and the hardness of raw water corresponding to the target geographical area is taken as target hardness of raw water of the water softening device.

The water softening device can determine the target geographical area where the water softening device is located through a positioning device of the water softening device, or when the water softening device is connected to the terminal, the water softening device can receive target geographical area information transmitted from the terminal is received.

In the method for determining the hardness of raw water of the water softening device, by determining the target hardness of raw water of the water softening device based on the target geographical area where the water softening device is located and the correspondence, defects such as cumbersome operations and inaccurate detection results caused by on-site testing of the hardness of raw water are avoided, and the efficiency and accuracy of determining the hardness of raw water are improved.

In an embodiment, the target hardness of raw water of the water softening device may be determined based on the target geographical area where the water softening device is located and the correspondence by:

determining, in accordance with a determination that no hardness of raw water matched with the target geographical area is included in the correspondence, a first geographical area closest to the target geographical area from the correspondence;

determining first hardness of raw water corresponding to a first geographical area from the correspondence based on the first geographical area; and assigning the first hardness of raw water to the target hardness of raw water.

After the target geographical area where the water softening device is located is determined, the water softening device will search the correspondence between the geographical area and the hardness of raw water for the hardness of raw water matched with the target geographical area. If no target geographical area is found in the correspondence between geographical area and the hardness of raw water, or the hardness data of raw water matched with the target geographical area is missing, the water softening device determines that no hardness of raw water matched with the target geographical area is included in the correspondence, and determines a first geographical area closest to the target geographical area from the correspondence between the geographical area and the hardness of raw water.

The water softening device then determines first hardness of raw water corresponding to a first geographical area from the correspondence between the geographical area and the hardness of raw water based on the first geographical area, and takes the first hardness of raw water as the target hardness of raw water of the water softening device.

For example, when the water softening device is located in County A, and the information of County A is not included in the correspondence between the geographical area and the hardness of raw water, the water softening device may find County B closest to County A as the first geographical area from the correspondence between the geographical area and the hardness of raw water. In one embodiment, although the information of County A is included in the correspondence between the geographical area and the hardness of raw water, the hardness information of raw water corresponding to County A is missing, the water softening device may find County B closest to County A, and take it as the first geographical area from the correspondence between the geographical area and the hardness of raw water.

The water softening device then determines first hardness of raw water B' corresponding to County B from the correspondence between the geographical area and the hardness of raw water; and takes the first hardness of raw water B' as the target hardness of raw water of the water softening device.

It can be understood that the hardness of raw water of County A is usually very close to that of County B since County A and County B are the closest.

In the method for determining the hardness of raw water of the water softening device, by assigning, in accordance with inability to determine the hardness of raw water of the geographical area where the water softening device is located, the hardness of raw water of the geographical area closest to the geographical area where the water softening device is located to the raw water of the water softening device, the hardness of raw water of the water softening device can still be very accurate, and the normal use of the water softening device is ensured.

In an embodiment, the target hardness of raw water of the water softening device is determined based on the target geographical area where the water softening device is located and the correspondence by:

determining, in accordance with a determination that no hardness of raw water matched with the target geographical area is included in the correspondence, second geographical areas that are within a preset distance range from the target geographical area from the correspondence;

determining second hardness of raw water corresponding to each of the second geographical areas from the correspondence based on each of the second geographical areas; and assigning an average value of all second hardness of raw water to the target hardness of raw water.

After the target geographical area where the water softening device is located is determined, the water softening device will search the correspondence between the geographical area and the hardness of raw water for the hardness of raw water matched with the target geographical area. If no target geographical area is found in the correspondence between geographical area and the hardness of raw water, or the hardness data of raw water matched with the target geographical area is missing, the water softening device determines that no hardness of raw water matched with the target geographical area is included in the correspondence, and determines second geographical areas that are within a preset distance range from the target geographical area from the correspondence between the geographical area and the hardness of raw water.

The water softening device then determines second hardness of raw water corresponding to each of the second geographical areas from the correspondence between the geographical area and the hardness of raw water based on each of the second geographical areas; and takes the average value of all second hardness of raw water as the target hardness of raw water of the water softening device.

For example, when the water softening device is located in City C, and information of City C is not included in the correspondence between the geographical area and the hardness of raw water, the water softening device may find City D, County E and City F within the preset distance range 100 km from City C as the second geographical areas from the correspondence between the geographical area and the hardness of raw water. In one embodiment, although the information of City C is included in the correspondence between the geographical area and the hardness of raw water, the hardness information of raw water corresponding to City C is missing, the water softening device may find City D, County E and City F within the preset distance range 100 km from City C, and taken them as the second geographical areas from the correspondence between the geographical area and the hardness of raw water.

The size of the preset distance range can be adjusted according to actual conditions. For example, the preset distance range may be 50 km, 100 km, etc., which is not specifically limited in the embodiments of the present disclosure.

The water softening device then determines second hardness of raw water D' corresponding to City D, second hardness of raw water E' corresponding to County E, and second hardness of raw water F corresponding to City F from the correspondence between the geographical area and the hardness of raw water. The water softening device then takes the average value (D'+E'+F')/3 of all second hardness of raw water as the target hardness of raw water of the water softening device.

It can be understood that the hardness of raw water of City C is very close to the average value of the hardness of raw water of City D, County E and City F, since City C is close to City D, County E and City F.

In the method for determining the hardness of raw water of the water softening device, by assigning, in accordance with inability to determine the hardness of raw water of the geographical area where the water softening device is located, the average value of the hardness of raw water of the geographical areas closest to the geographical area where the water softening device is located to the raw water of the water softening device, the hardness of raw water of the water softening device can still be very accurate, and the normal use of the water softening device is ensured.

In an embodiment, the target hardness of raw water of the water softening device may be determined based on the target geographical area where the water softening device is located and the correspondence by:

determining, in accordance with a determination that no hardness of raw water matched with the target geographical area is included in the correspondence, second geographical areas that are within a preset distance range from the target geographical area from the correspondence;

determining a third geographical area among second geographical areas, and determining third hardness of raw water corresponding to the third geographical area from the correspondence based on the third geographical area; and assigning the third hardness of raw water to the target hardness of raw water.

After the target geographical area where the water softening device is located is determined, the water softening device will search the correspondence between the geographical area and the hardness of raw water for the hardness of raw water matched with the target geographical area. If no target geographical area is found in the correspondence between geographical area and the hardness of raw water, or the hardness data of raw water matched with the target geographical area is missing, the water softening device determines that no hardness of raw water matched with the target geographical area is included in the correspondence, and determines second geographical areas that are within a preset distance range from the target geographical area from the correspondence between the geographical area and the hardness of raw water.

The water softening device then determines a third geographical area among second geographical areas, determines third hardness of raw water corresponding to the third geographical area from the correspondence between the geographical area and the hardness of raw water based on the third geographical area, and takes the third hardness of raw water as the target hardness of raw water of the water softening device.

For example, when the water softening device is located in City C, and the information of City C is not included in the correspondence between the geographical area and the hardness of raw water, the water softening device may find City D, County E and City F within the preset distance range 100 km from City C as the second geographical areas from the correspondence between the geographical area and the hardness of raw water. In one embodiment, although the information of City C is included in the correspondence between the geographical area and the hardness of raw water, the hardness information of raw water corresponding to City C is missing, the water softening device may find City D, County E and City F within the preset distance range 100 km from City C as the second geographical areas from the correspondence between the geographical area and the hardness of raw water.

The water softening device may then determine one of the second geographical areas City D, County E and City F as the third geographical area.

Assuming that the water softening device determines County E as the third geographical area among the second geographical areas City D, County E and City F, the water softening device determines the third hardness of raw water E' corresponding to County E from the correspondence between the geographical area and the hardness of raw water, and takes the third hardness of raw water E' as the target hardness of raw water of the water softening device.

It can be understood that the hardness of raw water of City C is very close to the hardness of raw water of City D, County E and City F, since City C is close to City D, County E and City F.

In the method for determining the hardness of raw water of the water softening device, by selecting, in accordance with inability to determine the hardness of raw water of the geographical area where the water softening device is located, one of the hardness of raw water of the geographical areas closest to the geographical area where the water softening device is located as the raw water of the water softening device, the hardness of raw water of the water softening device can still be very accurate, and the normal use of the water softening device is ensured.

In an embodiment, the third geographical area from second geographical areas, may be determined by any one of the following blocks.

1. a third geographic area is determined randomly from second geographic areas.

It can be understood that by randomly selecting one of the second geographical areas as the third geographical area, the target hardness of raw water of the water softening device can be quickly determined, which ensures the accuracy of the target hardness of raw water, and effectively saves system resources.

2. A second geographical area that meets a preset condition among the second geographical areas is assigned to the third geographical area, where the preset condition may include any one of the followings:

a raw water supplier in the second geographical area is the same as a raw water supplier in the target geographical area; and a raw water source in the second geographical area is the same as a raw water source in the target geographical area;

It should be noted that, under normal circumstances, the raw water of water softening device often uses domestic tap water, and the raw water supplier can be a water plant that provides domestic tap water.

When the raw water supplier in the second geographical area is the same as the raw water supplier in the target geographical area, considering that the raw water supplier has consistent raw water processing procedures, the hardness of the raw water of the second geographical area is the essentially same as that of the raw water of the target geographical area.

Raw water source refers to the source of raw water. For example, when the raw water is tap water, the raw water source can be rivers, lakes, groundwater, etc.

When the water source in the second geographical area is the same as the water source in the target geographical area, considering that the water hardness of the same water source should be consistent, the hardness of the raw water of the second geographical area is essentially the same as that of the raw water of the target geographical area.

It can be understood that, by selecting, from the second geographic areas, a second geographic area in which the raw water supplier is the same as the raw water supplier in the target geographical area, or the raw water source is the same as the raw water source in the target geographical area as the third geographical area, the final determined hardness of raw water of the water softening device can still have high accuracy, and the normal use of the water softening device is ensured.

In an embodiment, the method for determining the hardness of raw water of the water softening device according to an embodiment of the present disclosure may further include the following:

- updated information of the correspondence between the geographical area and the hardness of raw water is obtained, and the correspondence between the geographical area and the hardness of raw water is updated with the updated information.

It can be understood that, in order to maintain the accuracy of the hardness of raw water and ensure the normal operation of a water softener, a water hardness server can receive uploaded a new detection result of the hardness of raw water of the geographical area in real time or periodically, and update the correspondence between the geographical area and the hardness of raw water in real time or periodically.

The new detection result of the hardness of raw water of the geographical area may be detection result of the hardness of raw water of the geographical area that are already in the correspondence between the geographical area and the hardness of raw water, or may be detection result of the hardness of raw water of the geographical area that are added to the correspondence between the geographical area and the hardness of raw water.

After the correspondence between the geographical area and the hardness of raw water is updated, the server can transmit updated information of the correspondence between the geographical area and the hardness of raw water to the water softening device. After receiving the updated information, the water softening device may update the stored correspondence between geographical area and the hardness of raw water with the updated information.

In one embodiment, after the correspondence between the geographical area and the hardness of raw water is updated, the server can transmit updated information of the correspondence between the geographical area and the hardness of raw water to a terminal. The terminal forwards the updated information to the water softening device, and the water softening device may update the stored correspondence between geographical area and the hardness of raw water with the updated information after receiving the updated information forwarded from the terminal.

In the method for determining the hardness of raw water of the water softening device, by obtaining updated information of the correspondence between the geographical area and the hardness of raw water, and updating the correspondence between the geographical area and the hardness of raw water with the updated information, the accuracy of the hardness of raw water may be maintained and the normal use of water softening device is ensured.

FIG. 2 is a schematic flow chart of the method for determining the hardness of raw water of the water softening device according to an embodiment of the present disclosure in a water softening device installation scenario. Referring to FIG. 2, the following installation scenario of water softening device is taken as an example to illustrate again the method for determining the hardness of raw water of the water softening device according to the embodiment of the present disclosure, the method includes the following blocks.

Block 210: the water softening device arrives at an installation location. The installation location may be any location in a scenario that requires water softening device, such as living room, kitchen, office, pantry, etc. The installer completes the installation of the water softening device and activates the Wi-Fi module of the water softening device and the water softening device can be accessed to a network smoothly.

Block 220: the water softening device establishes a network connection with a water hardness server and receives the correspondence between the geographical area and the hardness of raw water transmitted from the water hardness server.

Block 230: the water softening device determines the target geographical area where the water softening device is located through the positioning device of the water softening device, and determines the target hardness of raw water of the water softening device from the correspondence between the geographical area and the hardness of raw water.

For the specific implementation of block 210 to block 230, reference may be made to the above embodiments of the method for determining the hardness of raw water of a water softening device, and details will not be described again here.

An embodiment of the present disclosure further provides an apparatus for determining hardness of raw water of a water softening device, and details will not be described again here.

Figure 3:
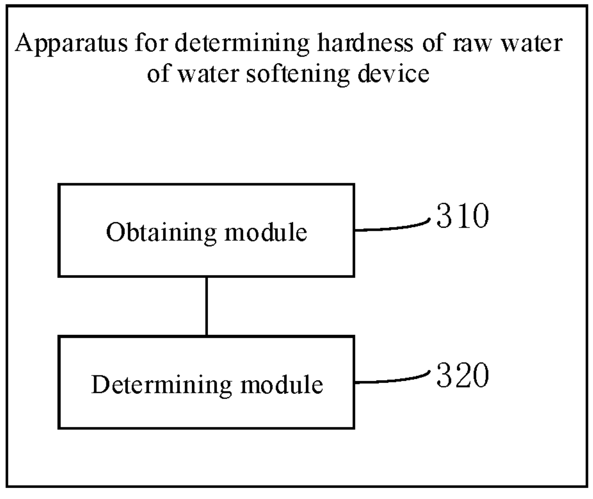
FIG. 3 is a schematic structural diagram of an apparatus for determining hardness of raw water of a water softening device according to an embodiment of the present disclosure.

FIG. 3 is a schematic structural diagram of an apparatus for determining hardness of raw water of a water softening device according to an embodiment of the present disclosure. Referring to FIG. 3, the apparatus for determining the hardness of raw water of water softening device may include:

- an obtaining device 310 for obtaining a correspondence between a geographical area and the hardness of raw water; and
- a determining device 320 for determining target hardness of raw water of the water softening device based on a target geographical area where the water softening device is located and the correspondence,
- where the correspondence is obtained by detecting hardness of raw water of respective geographical areas and associating each of the respective geographical areas with a detection result of the hardness of raw water corresponding to each of the respective geographical areas.

In the apparatus for determining the hardness of raw water of the water softening device, by determining the target hardness of raw water of the water softening device based on the target geographical area where the water softening device is located and the correspondence, defects such as cumbersome operations and inaccurate detection results caused by on-site testing of the hardness of raw water are avoided, and the efficiency and accuracy of determining the hardness of raw water are improved.

In an embodiment, the determining device 320, may be used for:

- determining, in accordance with a determination that no hardness of raw water matched with the target geographical area is included in the correspondence, a first geographical area closest to the target geographical area from the correspondence;
- determining first hardness of raw water corresponding to a first geographical area from the correspondence based on the first geographical area; and assigning the first hardness of raw water to the target hardness of raw water.

In an embodiment, the determining device 320, may be used for:

determining, in accordance with a determination that no hardness of raw water matched with the target geographical area is included in the correspondence, second geographical areas that are within a preset distance range from the target geographical area from the correspondence;

determining second hardness of raw water corresponding to each of the second geographical areas from the correspondence based on each of the second geographical areas; and assigning an average value of all second hardness of raw water to the target hardness of raw water.

In an embodiment, the determining device 320, may be used for:

determining, in accordance with a determination that no hardness of raw water matched with the target geographical area is included in the correspondence, second geographical areas that are within a preset distance range from the target geographical area from the correspondence;

determining a third geographical area among second geographical areas, and determining third hardness of raw water corresponding to the third geographical area from the correspondence based on the third geographical area; and assigning the third hardness of raw water to the target hardness of raw water.

In an embodiment, the determining device 320, may be used for:

determining, randomly, a third geographic area from second geographic areas; and assigning a second geographical area that meets a preset condition among the second geographical areas to the third geographical area, where the preset condition includes any one of the followings:

a raw water supplier in the second geographical area is the same as a raw water supplier in the target geographical area; and a raw water source in the second geographical area is the same as a raw water source in the target geographical area;

In an embodiment, the obtaining device 310, may be used for:

receiving the correspondence between the geographical area and the hardness of raw water transmitted from a server; and receiving the correspondence between the geographical area and the hardness of raw water transmitted from a terminal.

In an embodiment, the apparatus for determining the hardness of raw water of the water softening device according to an embodiment of the present disclosure further includes an updating device (not shown), which is used for:

obtaining updated information of the correspondence between the geographical area and the hardness of raw water, and updating the correspondence between the geographical area and the hardness of raw water with the updated information.

Figure 4:
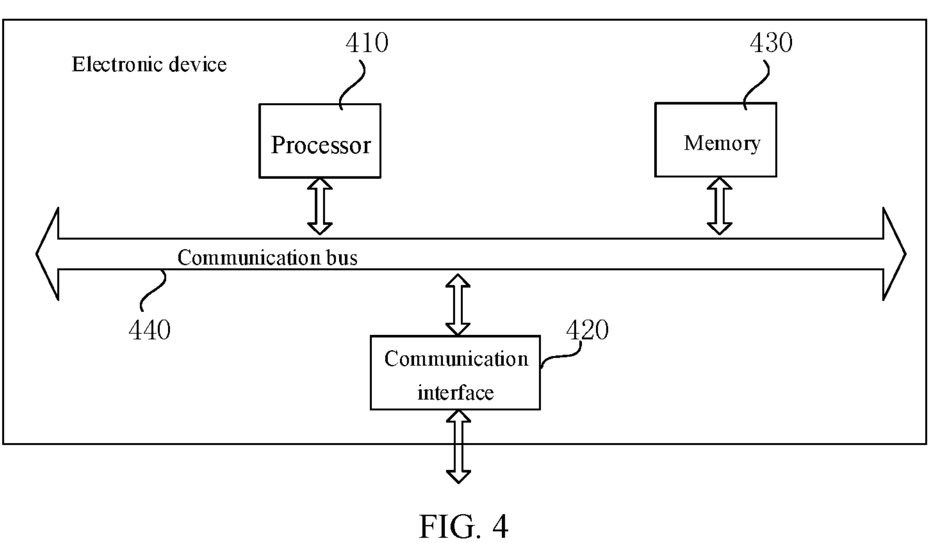
FIG. 4 is a schematic structural diagram of an electronic device according to an embodiment of the present disclosure.

FIG. 4 is a schematic diagram of the physical structure of an electronic device. As shown in FIG. 4, the electronic device may include a processor 410, a communication interface 420, a memory 430 and a communication bus 440. The processor 410, the communication interface 420 and the memory 430 communicate with each other through the communication bus 440. The processor 410 may call the logic instructions in the memory 430 to perform the following method, the method includes the following.

A correspondence between a geographical area and the hardness of raw water is obtained.

Target hardness of raw water of the water softening device is determined based on a target geographical area where the water softening device is located and the correspondence.

The correspondence is obtained by detecting hardness of raw water of respective geographical areas and associating each of the respective geographical areas with a detection result of the hardness of raw water corresponding to each of the respective geographical areas.

In addition, the logic instructions in the memory 430 described above may be implemented in the form of a software functional unit and may be stored in a computer readable storage medium when being sold or used as a separate product. Based on such understanding, the solution of the present disclosure or a part of the solution, which is essential or contributes to the prior art, may be embodied in the form of a software product, which is stored in a storage medium, including several instructions to cause a computer device (which may be a personal computer, a server, or a network device, etc.) to perform all or part of the blocks of the methods described in various embodiments of the present disclosure. The storage medium described above includes various media that can store program codes such as a flash disk, a mobile hard disk, a read-only memory (ROM), a random access memory (RAM), a magnetic disk, or an optical disk.

An embodiment of the present disclosure provides a computer program product, including: computer programs stored on a non-transient computer readable storage medium, and the computer programs include program instructions, when executed by a computer, causing the computer to perform the method described above. The method includes the following.

A correspondence between a geographical area and the hardness of raw water is obtained.

Target hardness of raw water of the water softening device is determined based on a target geographical area where the water softening device is located and the correspondence.

The correspondence is obtained by detecting hardness of raw water of respective geographical areas and associating each of the respective geographical areas with a detection result of the hardness of raw water corresponding to each of the respective geographical areas.

An embodiment of the present disclosure provides a non-transitory computer-readable storage medium having stored thereon computer programs, that, when executed by a processor, causes the processor to perform the method mentioned in above embodiments, and the method includes the following.

A correspondence between a geographical area and the hardness of raw water is obtained.

Target hardness of raw water of the water softening device is determined based on a target geographical area where the water softening device is located and the correspondence.

The correspondence is obtained by detecting hardness of raw water of respective geographical areas and associating each of the respective geographical areas with a detection result of the hardness of raw water corresponding to each of the respective geographical areas.

The device embodiments described above are merely illustrative, where the units described as separate components may or may not be physically separate, and the components displayed as units may or may not be physical units, that is, may be located at the same place, or can be distributed to multiple network units. Some or all of the modules may be selected according to actual needs to achieve the purpose of the solution of the present embodiment.

Through the description of the embodiments above, those skilled in the art can clearly understand that the various embodiments can be implemented by means of software and a necessary general hardware platform, and by hardware. Based on such understanding, the embodiment of the present application or a part of the embodiments, which is essential or contributes to the related art, may be embodied in the form of a software product, which is stored in a storage medium such as a ROM/RAM, a magnetic disk, an optical disk, etc., including several instructions to cause a computer device (which may be a personal computer, server, or network device, etc.) to perform various embodiments or a part of the methods described in various embodiments.

What is claimed is:

1. A method for determining hardness of raw water of a water softening device, comprising:

obtaining a correspondence between a geographical area and the hardness of raw water; and determining target hardness of raw water of the water softening device based on a target geographical area where the water softening device is located and the correspondence, wherein the correspondence is obtained by detecting hardness of raw water of respective geographical areas and associating each of the respective geographical areas with a detection result of the hardness of raw water corresponding to each of the respective geographical areas, wherein determining the target hardness of raw water of the water softening device based on the target geographical area where the water softening device is located and the correspondence comprises:

determining, in accordance with a determination that no hardness of raw water matched with the target geographical area is included in the correspondence, a first geographical area closest to the target geographical area from the correspondence;

determining first hardness of raw water corresponding to a first geographical area from the correspondence based on the first geographical area; and assigning the first hardness of raw water to the target hardness of raw water.

2. The method of claim 1, wherein determining the target hardness of raw water of the water softening device based on the target geographical area where the water softening device is located and the correspondence further comprises:

determining, in accordance with the determination that no hardness of raw water matched with the target geographical area is included in the correspondence, a plurality of second geographical areas that are within a preset distance range from the target geographical area from the correspondence;

determining second hardness of raw water corresponding to each of the plurality of second geographical areas from the correspondence based on each of the plurality of second geographical areas; and assigning an average value of all second hardness of raw water to the target hardness of raw water.

3. The method of claim 1, wherein the determining the target hardness of raw water of the water softening device based on the target geographical area where the water softening device is located and the correspondence further comprises:

determining, in accordance with the determination that no hardness of raw water matched with the target geographical area is included in the correspondence, a plurality of second geographical areas that are within a preset distance range from the target geographical area from the correspondence;

determining a third geographical area among the plurality of second geographical areas, and determining third hardness of raw water corresponding to the third geographical area from the correspondence based on the third geographical area; and assigning the third hardness of raw water to the target hardness of raw water.

4. The method of claim 3, wherein determining the third geographical area from the plurality of second geographical areas comprises any one of the following:

determining, randomly, a third geographic area from a plurality of second geographic areas; and assigning a second geographical area that meets a preset condition among the plurality of second geographical areas to the third geographical area, wherein the preset condition comprises any one of the following:

a raw water supplier in the second geographical area is the same as a raw water supplier in the target geographical area; and a raw water source in the second geographical area is the same as a raw water source in the target geographical area.

5. The method of claim 1, wherein obtaining the correspondence between the geographical area and the hardness of raw water comprises any one of the following:

receiving the correspondence between the geographical area and the hardness of raw water transmitted from a server; and receiving the correspondence between the geographical area and the hardness of raw water transmitted from a terminal.

6. The method of claim 1, further comprising:

obtaining updated information of the correspondence between the geographical area and the hardness of raw water, and updating the correspondence between the geographical area and the hardness of raw water with the updated information.

7. An apparatus for determining hardness of raw water of a water softening device, comprising:

an obtaining device for obtaining a correspondence between a geographical area and the hardness of raw water; and a determining device for determining target hardness of raw water of the water softening device based on a target geographical area where the water softening device is located and the correspondence, wherein the correspondence is obtained by detecting hardness of raw water of respective geographical areas, and associating each of the respective geographical areas with a detection result of the hardness of raw water corresponding to each of the respective geographical areas, wherein the determining device is configured to:

determine, in accordance with a determination that no hardness of raw water matched with the target geographical area is included in the correspondence, a first geographical area closest to the target geographical area from the correspondence;

determine first hardness of raw water corresponding to a first geographical area from the correspondence based on the first geographical area; and assign the first hardness of raw water to the target hardness of raw water.

8. An electronic device, comprising a memory, a processor, and a computer program stored on the memory and executable on the processor, wherein the computer program, when executed by a processor, causes the electronic device to perform the method for determining hardness of raw water of a water softening device of claim 1.

9. A non-transitory computer-readable storage medium having a computer program stored thereon, wherein the computer program, when executed by a processor, causes the processor to perform the method for determining hardness of raw water of a water softening device of claim 1.

10. A computer program product, having a computer program, wherein the computer program, when executed by a processor, causes the processor to perform the method for determining hardness of raw water of a water softening device, which causes the processor to:

obtain a correspondence between a geographical area and the hardness of raw water; and determine target hardness of raw water of the water softening device based on a target geographical area where the water softening device is located and the correspondence, wherein the correspondence is obtained by detecting hardness of raw water of respective geographical areas and associating each of the respective geographical areas with a detection result of the hardness of raw water corresponding to each of the respective geographical areas, wherein determining target hardness of raw water of the water softening device based on a target geographical area where the water softening device is located and the correspondence comprises:

determining, in accordance with a determination that no hardness of raw water matched with the target geographical area is included in the correspondence, a first geographical area closest to the target geographical area from the correspondence;

determining first hardness of raw water corresponding to a first geographical area from the correspondence based on the first geographical area; and assigning the first hardness of raw water to the target hardness of raw water.

11. The computer program product of claim 10, wherein determining the target hardness of raw water of the water softening device based on the target geographical area where the water softening device is located and the correspondence further causes the processor to:

determine, in accordance with the determination that no hardness of raw water matched with the target geographical area is included in the correspondence, a plurality of second geographical areas that are within a preset distance range from the target geographical area from the correspondence;

determine second hardness of raw water corresponding to each of the plurality of second geographical areas from the correspondence based on each of the plurality of second geographical areas; and assign an average value of all second hardness of raw water to the target hardness of raw water.

12. The computer program product of claim 10, wherein the determining the target hardness of raw water of the water softening device based on the target geographical area where the water softening device is located and the correspondence further causes the processor to:

determine, in accordance with the determination that no hardness of raw water matched with the target geographical area is included in the correspondence, a plurality of second geographical areas that are within a preset distance range from the target geographical area from the correspondence;

determine a third geographical area among the plurality of second geographical areas, and determining third hardness of raw water corresponding to the third geographical area from the correspondence based on the third geographical area; and assign the third hardness of raw water to the target hardness of raw water.

13. The computer program product of claim 12, wherein determining the third geographical area from the plurality of second geographical areas further causes the processor to perform any one of the following:

determine, randomly, a third geographic area from the plurality of second geographic areas; and assign a second geographical area that meets a preset condition among the plurality of second geographical areas to the third geographical area, wherein the preset condition comprises any one of the following:

a raw water supplier in the second geographical area is the same as a raw water supplier in the target geographical area; and a raw water source in the second geographical area is the same as a raw water source in the target geographical area.

14. The computer program product of claim 10, wherein obtaining the correspondence between the geographical area and the hardness of raw water further causes the processor to perform any one of the following:

receive the correspondence between the geographical area and the hardness of raw water transmitted from a server; and receive the correspondence between the geographical area and the hardness of raw water transmitted from a terminal.

15. The computer program product of claim 10, wherein the computer program, when executed by the processor, further causes the processor to:

obtain updated information of the correspondence between the geographical area and the hardness of raw water; and update the correspondence between the geographical area and the hardness of raw water with the updated information.

* * * * *